United States Patent [19]

Berger

[11] 4,018,930

[45] Apr. 19, 1977

[54] SUBSTITUTED INDOLOBENZAZEPINES

[75] Inventor: Joel G. Berger, Freeport, N.Y.

[73] Assignee: Endo Laboratories, Inc., Garden City, N.Y.

[22] Filed: July 17, 1975

[21] Appl. No.: 596,851

Related U.S. Application Data

[63] Continuation-in-part of Ser. No. 422,615, Dec. 6, 1973, abandoned.

[52] U.S. Cl. .......................... 424/267; 260/293.55
[51] Int. Cl.$^2$ ...................................... C07D 471/16
[58] Field of Search ............... 260/293.55; 424/267

[56] References Cited

UNITED STATES PATENTS

| | | | |
|---|---|---|---|
| 3,373,153 | 3/1968 | Cohen et al. | 260/239 |
| 3,373,168 | 3/1968 | Cohen et al. | 260/293 |
| 3,890,327 | 6/1975 | Berger | 260/293.55 |
| 3,932,650 | 1/1976 | Adams | 424/267 |

*Primary Examiner*—G. Thomas Todd

[57] ABSTRACT

Certain trans-1,2,3,4,4a,8,9,14a-octahydropyrido-[4',-3':2,3]indolo[1,7-ab][1]benzazepines substituted at the 3-position with (a) certain unsaturated organic radicals, prepared by alkylation or acylation/reduction of the corresponding unsubstituted compound or (b) cis-2,3-dimethylcyclopropyl)methyl, prepared by hydrogenation of the corresponding 3-(2,3-dimethylcycloprop-2-en-1-yl)methyl compound. The compounds are useful as analgesics and sedative-tranquilizers.

16 Claims, No Drawings

SUBSTITUTED INDOLOBENZAZEPINES

CROSS-REFERENCE TO RELATED APPLICATION

This application is a continuation-in-part of copending U.S. Patent Application Ser. No. 422,615, filed Dec. 6, 1973, now abandoned.

BACKGROUND OF THE INVENTION

This invention relates to octahydropyridoindolobenzazepines.

Certain octahydropyridoindolobenzazepines are known from U.S. Pat. Nos. 3,373,168 and 3,457,271, assigned to Hoffmann-La Roche, Inc. Those compounds can be represented according to the above-mentioned patents by the following Formula (1):

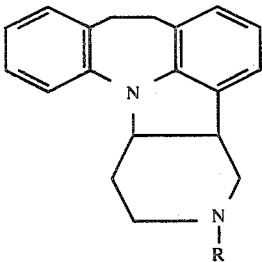

wherein R is a straight chain or branched alkyl having 1–7 carbon atoms.

According to the IUPAC 1957 Rules, the same compounds are represented by the formula:

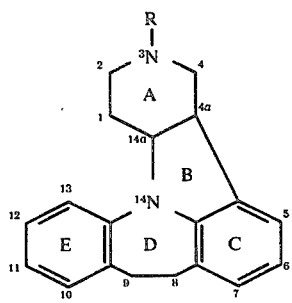

and are named 1,2,3,4,4a,8,9,14a-octahydropyrido[4′,3′:2,3]indolo[1,7-ab][1]benzazepines. The IUPAC representation and nomenclature will be used herein.

The compounds of Formula (1) are said 1,2,3,4,4U.S. 8,9,14a-octahydropyrido3,373,168 and 3,457,271 to have antidepressant activity and to be useful antidepressant agents. These compounds are prepared according to the above two patents by reduction of the corresponding hexahydro compounds either with sodium in a mixture of tetrahydrofuran and liquid ammonia or with zinc in hydrochloric acid. The former method is preferred by the patentees since it gives higher yields.

U.S. application of C. D. Adams, Ser. No. 422,616, filed Dec. 6, 1973, which is a continuation-in-part of U.S. Application Ser. No. 325,352, filed Jan. 22, 1973 and now abandoned, discloses 1,2,3,4,4a,8,9,14a-octahydropyrido[4′,3′:2,3]indolo[1,7-ab][1]-benzazepines which can be represented by structural formula 1 wherein R is $C_1$-$C_4$ alkyl, $C_3$-$C_6$ cycloalkyl, $C_4$-$C_7$ cycloalkylmethyl, exo-7-norcarylmethyl, benzyl or phenethyl. The compounds of the application have a different steric configuration of the hydrogen atoms at the 4a and 14a positions from those of the above patents. The evidence is that the compounds of the application have the transconfiguration of the 4a and 14a hydrogens and that the compounds of the above patents have the cis configuration. The compounds of the application are made by reducing the corresponding hexahydro compounds with boron hydride/tetrahydrofuran complex in tetrahydrofuran or diethyleneglycol dimethyl ether, and are useful as CNS depressants analgesics.

U.S. Application Ser. No. 359,504, filed May 11, 1973, now U.S. Pat. No. 3,890,327, granted June 17, 1975, discloses trans-1,2,3,4,4a,8,9,14a-octahydropyrido]4′,3′:2,3]indolo[1,7-ab][1]-benzazepine and its use as an analgesic. This compound is sometimes hereinafter referred to as "the nor compound".

SUMMARY OF THE INVENTION

It has now been discovered that certain 3-substituted derivatives which can only be made by processes involving alkylation or acylation/reduction of the nor compound are useful analgesics and sedative/tranquilizers. The compounds can be represented by the formula:

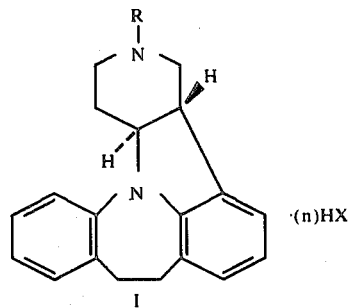

wherein n is zero or one;

X is the anion of a pharmaceutically suitable acid; and

R is 3-chloro-2-butenyl; 2-bromoallyl; $C_3$-$C_8$ oxoalkyl side chain; phenacyl; 3-oxo-3-phenylpropyl; $C_3$-$C_5$ alkenyl; $C_3$-$C_5$ alkynyl; cinnamyl; cinnamyl ring-substituted with chloro, bromo or methoxy; 3-phenyl-2-propynyl; (cis-2,3-dimethyl-cyclopropyl)-methyl; $C_6$-$C_8$ cycloalkenylmethyl; $C_6$-$C_8$ cycloalkadienylmethyl; (2,3-dimethylcycloprop-2-en-1-yl)methyl; (cis-1,6-dimethyl-endo-3-norcaren-7-yl)methyl; (4-methylbicylco[[2.2.2]-oct-2-en-1-yl)methyl; or (bicyclo[2.2.1]hept-2-en-5-yl)methyl;

and the hydrogens in the 4a and 14a positions are in trans-relationship to each other.

This invention includes the compounds of formula I, pharmaceutically compositions containing them, their use as analgesics and sedative/tranquilizers, and the processes for making them described below.

DETAILED DESCRIPTION OF THE INVENTION

Preferred Compounds

Certain compounds of formula I are preferred because of more desirable pharmacological profile and/or because of greater ease of synthesis. In particular, those compounds of formula I are preferred where:

R is 3-chloro-2-butenyl; $C_3$-$C_8$ oxoalkyl side chain; phenacyl; 3-oxo-3-phenylpropyl; $C_3$-$C_5$ alkenyl; $C_3$-$C_5$ alkynyl; or $C_6$-$C_8$ cycloalkenylmethyl.

More preferred are those compounds where:

R is 3-chloro-2-butenyl; $C_3$-$C_8$ ketoalkyl side chain; phenacyl; 3-oxo-3-phenylpropyl; $C_3$-$C_5$ alkenyl; $C_3$-$C_5$ alkynyl; or $C_6$-$C_8$ cycloalkenylmethyl.

Especially preferred are those compounds where: R is a $C_3$-$C_5$ ketoalkyl side chain; phenacyl; or 3-oxo-3-phenylpropyl; in particular:

(±)-1-immediately trans-1,2,3,4,4a,8,9,14a-octahydropyrido[4',3':2,3]indolo[1,7-ab][1]benzazepin-3-yl)-2-propanone (±)-4-(trans-1,2,3,4,4a,8,9,14a-octahydropyrido[4',3':2,3]indolo[1,7-ab][1]benzazepin-3-yl)-2-butanone (±)-5-(trans-1,2,3,4,4a,8,9,14a-octahydropyrido[4',3':2,3]indolo[1,7-ab][1]benzazepin-3-yl)-2-pentanone (±)-3-(trans-1,2,3,4,4a,8,9,14a-octahydropyrido[4',3':2,3]indolo[1,7-ab][1]benzazepin-3-yl)propiophenone

Synthesis

Compounds of formula I can be made by alkylation of the nor compound (formula II) in presence of an acid acceptor:

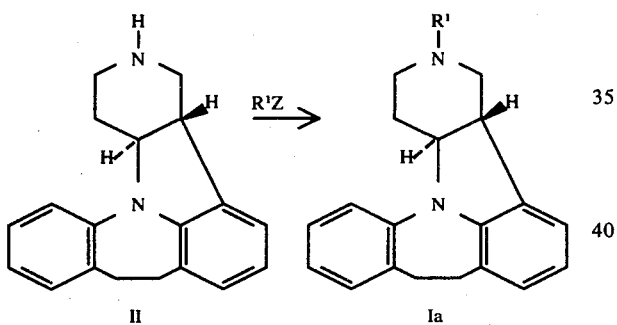

wherein $R^1$ is R as defined above excluding (cis-2,3-dimethylcyclopropyl)methyl; and Z is —Cl, —Br, —I or —OS(O)$_2$R$^2$, where $R^2$ is methyl, phenyl, or p-tolyl;

and then optionally converting the free base (formula Ia) to a salt by reaction with a pharmaceutically suitable acid. The alkylation reaction is carried out in a polar organic solvent such as dimethylformamide, dimethyl sulfoxide, hexamethylphosphoramide, acetone, methyl ethyl ketone, methanol or ethanol, in the presence of an alkali metal or alkaline earth metal carbonate or bicarbonate, or a tertiary amine, for example pyridine or triethylamine. Reaction temperatures in the range of 0° to 100° C. can be used; preferred range is 20° to 40° C.

Compounds of formula I can also be made by acylation of the nor compound followed by reduction with a metal hydride reducing agent such as lithium aluminum hydride or sodium bis(2-methoxyethoxy)aluminum hydride:

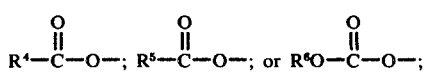

wherein $R^4$ is 2-chloro-1-propenyl; 1-bromovinyl; $C_2$-$C_4$ alkenyl; $C_2$-$C_4$ alkynyl; $C_3$-$C_7$ cycloalkenyl; $C_3$-$C_7$ cycloalkadienyl; 2,3-dimethylcycloprop-2-en-1-yl; cis-1,6-dimethyl-endo-3-norcaren-7-yl; 4-methylbicyclo[2.2.2]oct-2-en-1-yl; or bicyclo[2.2.1]hept-2-en-5-yl;

Q is —Cl; —Br; $C_1$-$C_4$ alkoxy;

$$R^4-\overset{O}{\underset{\|}{C}}-O-;\ R^5-\overset{O}{\underset{\|}{C}}-O-;\ \text{or}\ R^6O-\overset{O}{\underset{\|}{C}}-O-;$$

$R^5$ is $C_1$-$C_4$ alkyl; and $R^6$ is $C_1$-$C_4$ alkyl;

$R^7$ is R as defined above, excluding $C_3$-$C_8$ oxoalkyl side chain phenacyl, 3-oxo-3-phenylpropyl, cinnamyl, substituted cinnamyl, 3-phenyl-2-propnynyl and (cis-2,3-dimethylcyclopropyl)methyl;

and then optionally converting the free base (formula Ib) to a salt by reaction with a pharmaceutically suitable acid. The acylating agent

is an acid halide (Q = Cl or Br), ester (Q=$C_1$-$C_4$ alkoxy), anhydride

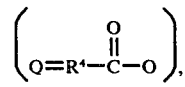

mixed anhydride

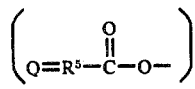

including mixed anhydrides with an ester of carbonic acid

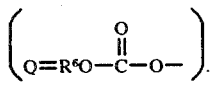

The acylation is carried out in an organic solvent such as benzene, chloroform or dichloromethane at a temperature of 0° to 80° C, preferably 0° to 40° C. When the acylating agent is an acid halide, an inorganic or tertiary amine base is present to react with liberated acid. The reduction is carried out with a conventional reducing agent such as lithium aluminum hydride in an ethereal solvent, such as tetrahydrofuran, glyme or diglyme, or sodium bis(2-methoxyethoxy) aluminum hydride in a solvent such as benzene or toluene, at a temperature in the range of 30° to 100° C, preferably 30° to 65° C. Glyme and diglyme are trivial names for ethylene glycol dimethyl ether and diethylene glycol dimethyl ether, respectively.

Compounds of formula I wherein R is (cis-2,3-dimethylcyclopropyl)methyl can be made by catalytic hydrogenation of a corresponding compound of formula I wherein R is (2,3-dimethylcycloprop-2-en-1-yl) methyl at temperatures in the range 20°–50° C.

In addition, the compounds of formula I wherein R is 3-oxybutyl can be made by Michael - like addition of methyl vinyl ketone to the nor compound in the presence of a suitable solvent, such as ethanol.

Representative pharmaceutically suitable acids which can be used to make the acid addition salts of this invention are the following: hydrochloric, hydrobromic, sulfuric, sulfamic, phosphoric, nitric, maleic, fumaric, benzoic, ascorbic, citric, pamoic, succinic, methanesulfonic, ethanedisulfonic, acetic, propionic, tartaric, salicylic, gluconic, lactic, malic, mandelic, cinnamic, citraconic, aspartic, stearic, palmitic, itaconic, glycolic, p-aminobenzoic, glutamic, and toluenesulfonic.

All compounds of formula I have at least two asymmetric centers, resulting from the reduction of the $\Delta^{4a,14a}$ to the trans-fused system. This invention includes the optically active enantiomers, as well as the racemic mixtures. In addition, if the 3-substituent includes a grouping capable of existing in stereoisomeric forms, all the resulting diastereoisomers are also included in this invention.

Intermediate

The nor compound, which is the key intermediate for obtaining the compounds of formula I, was prepared by the following procedure:

A mixture of 24.6 g of N-aminoiminodibenzyl (5-amino-10,11-dihydro-5H-dibenz[b,f]azepine) and 14.8 g of 4-piperidone hydrochloride in 250 ml. ethanol was heated on a steam bath for 15 minutes and cooled; a solution of 20 g. of concentrated sulfuric acid in 250 ml. ethanol was added. The resulting mixtue was reheated on the steam bath for an additional 40 minutes: the solution which formed was cooled, basified with ammonia, and diluted with 1 liter of water. The crude, semisolid material which separated was taken up in ether, and the aqueous mother liquors were extracted with additional portions of ether. The combined ethereal extracts were concentrated to 500 ml. and treated, under an atmosphere of nitrogen and with vigorous stirring, with 50 ml. of 5N hydrochloric acid. The resulting precipitate was filtered off, washed with ether and C (dec). 1N hydrochloric acid, and dried in vacuo at 100° to yield 1,2,3,8,9-hexahydropyrido[4',3':2,3]indolo[1,7-ab][1-]benzazepine hydrochloride, m.p. 309°, a salt only very slightly soluble in water. Dissolving the above salt in aqueous acetic acid, basifying with ammonia, filtering off the crude product and recrystallizing it from benzene regenerated the free 1,2,3,4,8,9-hexahydropyrido[4',3':2,3]indolo[1,7-ab][1]benzazepine, m.p. 134°–136° C.

To a solution of 16.4 g of 1,2,3,4,8,9-hexahydropyrido[4',3':2,3]indolo[1,7-ab][1]benzazepine in 500 ml. of dichloromethane, 7.3 g. of cyclopropanecarbonyl chloride was added, followed by dropwise addition of 10 ml. of triethylamine. A mildly exothermic reaction took place, after which stirring of the mixture was continued at room temperature overnight. The mixture was then washed with 1N hydrochloric acid and water and dried over anhydrous sodium carbonate. On evaporation to dryness, crude 3-(cyclopropylcarbonyl)-1,2,3,4,8,9-hexahydropyrido[4',3':2,3]indolo[1,7-ab][1]benzazepine was obtained as a glassy product. Recrystallization from ethanol yielded the pure material, m.p. 154°–156° C.

A solution of 8.6 g. of the above compound in 120 ml. of tetrahydrofuran was added dropwise to a suspension of 2.3 g. of lithium aluminum hydride in 180 ml. of tetrahydrofuran. On completion of the addition, the mixture was first refluxed for four hours, then allowed to stir at room temperature overnight and finally decomposed in the usual manner. After filtering off the inorganic salts, the filtrate was dried over anhydrous sodium carbonate and evaporated in vacuo; the residue was dissolved in a 1:1 mixture of ethyl acetate-benzene and chromatographed on a 14 × 2.2 cm. column of basic alumina, activity I. The eluate was taken down to dryness; the residual oil dissolved in absolute alcohol, saturated with ethanolic hydrogen chloride, and once again evaporated to dryness. Upon crystallization of the residue from acetone, 3-(cyclopropylmethyl)-1,2,3,4,8,9-hexahydropyrido[4',3':2,3]indolo[1,7-ab][1]benzazepine hydrochloride, m.p. 267°, was obtained.

A solution of 9.25 g. of the free base of the above hexahydro compound in 75 ml. of tetrahydrofuran was added dropwise to a stirred 1N-solution of boron hydride in tetrahydrofuran (100 ml.) under a nitrogen blanket. After the addition was complete, the mixture was refluxed under nitrogen for five hours, then cooled in ice and quenched with 20 ml. of 6N hydrochloric acid. The mixture was distilled, the removed liquid being from time to time replaced by addition of dioxane. The mixture was again refluxed at 91° C. for 1 hour with additional 6N hydrochloric acid, then cooled to 70° C., made basis with sodium hydroxide, and evaporated in vacuum. The semisolid residue was treated with water and chloroform, and the chloroform layer was further worked up to yield (±)-trans-3-cyclopropylmethyl)-1,2,3,4a,8,9,14a-octahydropyrido[4',-

3':2,3]indolo[1,7-*ab*][1]benzazepine, m.p. 152.5°–155° after recrystallization from ether.

A solution of 4.2 ml. of ethyl chloroformate in 35 ml. dry benzene was added to a solution of 3.9 grams (±)-trans-3-(cyclopropylmethyl)-1,2,3,4,4*a*,8,9,14*a*-octahydropyrido[4'3':2,3]indolo[1,7-ab][1]benzazepine in 100 ml. dry benzene. The stirred solution was heated to reflux whereupon a white precipitate formed. Heating at reflux was continued for 3½ hours and the reaction mass was cooled and filtered; 0.43 grams of solids were collected. Filtrate was evaporated to dryness leaving a heavy yellow oil. This was dissolved in 100 ml. n-butanol, 10 grams KOH pellets were added and the mixture was stirred at reflux for 1 hour. The mass was then cooled and concentrated and the residue was partitioned between toluene and water. The toluene solution was then extracted with water until the extracts were neutral, then the toluene solution was extracted four times with 100 ml. of 2N aqueous tartaric acid. The combined extracts were washed once with ether then basified with sodium hydroxide. The oily product was extracted twice into methylene chloride. The combined extracts were washed and dried over potassium carbonate. The solution was then filtered and evaporated to get a pale, yellow oil which crystallized under pentane. Recrystallization from about 50 ml. hexane/benzene gave 1.68 grams (±)-trans-1,2,3,4,,4*a*,8,9,14*a*-octahydropyrido[4',3':2,-3]indolo[1,7-ab][1]benzazepine, yellow crystals melting point 148.5°–149.5° C.

Preparation of the compounds of this invention is illustrated by the following examples, wherein all parts, proportions, and percentages are by weight, unless otherwise indicated.

EXAMPLE 1

(±)-trans-3-(3-chloro-2-butenyl)-1,2,3,4,4*a*,8,9,14*a*-octahydropyrido[4',3':2,3]indolo[1,7-ab][1]benzazepine A suspension of 2.76 g of (±)-trans-1,2,3,4,4*a*,8,9,-14*a*-octahydropyrido[4',3';2,3]indolo[1,7-ab][1]benzazepine in 20 ml of dimethylformamide (DMF) containing 2.3 ml triethylamine was treated with 1.25 g of 1,3-dichloro-2-butene. Solution resulted immediately. The solution was stirred at room temperature for 4 hours, by which time some white precipitate had formed. The reaction mixture was poured into 150 ml of cold water, a gummy solid was separated and washed by decantation with cold water. Recrystallization from ethanol gave 2.93 g of the title compound, m.p. 130°–132° C.

EXAMPLE 2

(±)-trans-1,2,3,4,4*a*,8,9,14*a*-octahydro-3-(2-propynyl)pyrido[4',3':2,3]indolo[1,7-ab][1]benzazepine Propargyl bromide, 2.38 g, was added to a solution of (±)-trans-1,2,3,4,4*a*,8,9,14a-octahydropyrido[4',3':2,-3]indolo[1,7-ab][1]benzazepine (5.52 g) and triethylamine (3ml) in 90 ml DMF. The reaction mixture was stirred at room temperature for 4½ hours. Some precipitate had formed. The reaction mixture was poured into 300 ml of cold water. A solid precipitated which was filtered off and washed with cold water. Recrystallization from 300 ml ethanol gave 4.05 g of the title compound as pale yellow needles, m.p. 160°–161.5°. An analytical sample was recrystallized again from ethanol to give almost colorless needles, m.p. 162°–163° C.

EXAMPLE 3

(±)-trans-3-acetonyl-1,2,3,4,4*a*,8,9,14*a*-octahydropyrido[4',3':2,3]indolo[1,7-*ab*][1]benzazepipine Triethylamine (5 ml) was added to a solution of 2.8 g pf (±)-trans-1,2,3,4,4*a*,8,9,14*a a*-octahydropyrido[-4',3':2,3]indolo[1,7-ab][1]benzazepine in 50 ml DMF, followed by addition of 1 g of chloroacetone in 5 ml DMF. The mixture was stirred for 3.5 hours at room temperature, poured into 100 ml water, then extracted with ether. The ether was washed with water, dried with Na$_2$SO$_4$, filtered, and evaporated to dryness in vacuo. The residue was dissolved in benzene, then chromatographed through basic alumina using benzene as eluant, to yield 1.5 g of the title compound with m.p. 128.5° (dec). An alternative name for the title compound is (±)-trans-1-(1,2,3,4,4*a*,8,9,14*a*-octahydropyrido[4',3':2,3]indolo[1,7-ab][1]benzazepin-3-yl)-2-propanone.

EXAMPLE 4

(±)-trans-3-allyl-1,2,3,4,4*a*,8,9,14*a*-octahydropyrido[-4',3':2,3]indolo[1,7-ab][1]benzazepine, hydrochloride Triethylamine (4.2 ml) was added to 2.8 g (±)-trans-1,2,3,4,4*a*,8,9,14*a*-octahydropyrido[4',3':2,3]indolo[1,7-ab][1]benzazepine in 50 ml DMF, followed by slow addition of 1.6 g of allyl bromide in 5 ml DMF. This was stirred at room temperature for 3.5 hours then poured in 125 ml water and extracted with ether. The ether was washed once with water, dried with Na$_2$SO$_4$ and evaporated to dryness in vacuo. The residue was dissolved in anhydrous ether and the title compound was precipitated by addition of hydrogen chloride. After recrystallization from acetone, m.p. of the product was 231°–232.5° C. (dec.)

EXAMPLE 5

(±)-trans-3-[(3-cyclohexen-1-yl)methyl]-1,2,3,4,4*a*,8,9,14*a*-octahydropyrido[4',3':2,3]indolo[1,7-ab][1]benzazepine Triethylamine (10 ml.) was added with stirring to a solution of 5.5 g. (±)-trans-1,2,3,4,4*a*,8,9,14*a*-octahydropyrido[4',3':2,3]indolo[1,7-ab][1]benzazepine in 100 ml. chloroform, followed by addition, with stirring, of 5.76 g. (0.04 moles) 3-cyclohexene-1-carbonyl chloride in 10 ml. chloroform. The mixture was refluxed 2 hours then cooled and water was added. The organic layer was separated, dried over K$_2$CO$_3$, and evaporated to dryness in vacuo. Trituration of the residual oil in hexane gave (±)-trans-3-[(3-cyclohexen-1-yl)carbonyl]-1,2,3,4,4*a*,8,9,14*a*-octahydropyrido[4',-3':2,3]indolo[1,7-ab][1]benzazepine, m.p. 156.5°–158.5°.

This amide (7.4 g., 0.02 moles) was dissolved in 200 ml. benzene and added to 34 ml. of a reducing agent in 200 ml. benzene, with stirring, under a nitrogen atmosphere. The reducing agent was a 70% solution of sodium bis(2-methoxyethoxy)aluminum hydride in benzene. The resulting mixture was refluxed for 2 hours, then decomposed by slow dropwise addition of 100 ml. aqueous 10% sodium hydroxide solution while cooling in an ice bath. The organic layer was washed with water until neutral, dried over K$_2$CO$_3$, filtered and evaporated to dryness to yield the title compound as a solid which, after trituration in hexane, melted at 154.7°–157.5°.

EXAMPLE 6

(±)-4-(trans-1,2,3,4,4a,8,9,14a-octahydropyrido[4′,-3′:2,3]indolo[1,7-ab][1]benzazepin-3-yl)-2-butanone 2.3 grams of methyl vinyl ketone was added to a solution of 8.3 grams of (±)-trans-1,2,3,4,4a,8,9,14a-octahydropyrido[4′,3′:2,3]indolo[1,7-ab][1]benzazepine in 400 ml. of ethanol. The mixture was permitted to stand at room temperature for four days, after which an additional 2.6 grams of methyl vinyl ketone was added. This mixture was permitted to stand at room temperature for three days, and was then filtered, evaporated to dryness in vacuo, and triturated with pentane. The resulting solid was recrystallized from ethanol to yield 9 grams of the title compound with m.p. 102.5° C.

EXAMPLE 7

(±)-5-(trans-1,2,3,4,4a,8,9,14a-octahydropyrido[4′,-3′:2,3]indolo[1,7-ab][1]benzazepin-3-yl)-2-pentanone 3.6 grams of potassium iodide and 12 ml. of triethylamine were added to a solution of 5.5 grams of (±)-trans-1,2,3,4,4a,8,9,14a-octahydropyrido[4′,3′:2,3]indolo[1,7-ab][1]benzazepine in 50 ml. DMF, followed by addition of 3.7 grams of 5-chloro-2-pentanone ethylene ketal. The mixture was heated at approximately 62° C for 20 hours. The mixture was then poured into water, extracted with benzene, and chromatographed through basic alumina to eliminate remaining benzazepine starting material. The resulting ketal was dissolved in ether. HCl gas was bubbled through this solution to precipitate the hydrochloride salt of the title compound. Recrystallization from ethanol yielded 350 mg. of the title compound, hydrochloride salt, m.p. 258°–259° C(dec).

EXAMPLE 8

(±)-3-(trans-1,2,3,4,4a,8,9,14a-octahydropyrido[4′,-3′:2,3]indolo[1,7-ab][1]benzazepin-3-yl)propiophenone 5.5 grams of (±)-trans-1,2,3,4,4a,8,9,14a-octahydropyrido[4′,3′:2,3]indolo[1,7-ab][1]benzazepine, 3.6 grams of potassium iodide, 6.5 ml of triethylamine and 4.2 grams of β-chloropropiophenone were suspended in 100 ml DMF and heated to 60° C for 2 hours. The mixture was permitted to cool to room temperature, poured into 200 ml. of water and extracted with benzene. The benzene layer was washed with water, dried over potassium carbonate, filtered and evaporated to dryness in vacuo. The resulting oil was taken up in ether and converted to the hydrochloride salt as in Example 7, thus yielding 6.7 grams of the title compound, hydrochloride salt, m.p. 279° C (dec).

The following additional compounds of formula I can be prepared by the process described in Examples 1–8 above.

1. (±)-trans-1,2,3,4,4a,8,9,14a-octahydro-3-[(4-methylbicyclo[2.2.2]oct-2-en-1-yl)methyl]pyrido[4′,-3′:2,3]indolo[1,7-ab][1]benzazepine
2. (±)-trans-3-(2-cyclohexen-1-yl)methyl-1,2,3,4,4a,8,9,14a-octahydropyrido[4′,3′:2,3]indolo[1,7-ab][1]benzazepine
3. (±)-trans-1,2,3,4,4a,8,9,14a-octahydro-3-[(2,3-dimethylcycloprop-2-en-1-yl)methyl]pyrido[4′,3′:2,-3]indolo[1,7-ab][1]benzazepine
4. (±)-trans-1,2,3,4,4a,8,9,14a-octahydro-3-(3-methyl-2-butenyl)pyrido[4′,3′:2,3]indolo[1,7-ab][1]benzazepine
5. (±)-3-(trans-2-butenyl)-1,2,3,4,4a,8,9,14a-octahydropyrido[4′,3′:2,3]indolo[1,7-ab][1]benzazepine
6. (±)-trans-3-(cis-2-butenyl)-1,2,3,4,4a,8,9,14a-octahydropyrido[4′,3′:2,3]indolo[1,7-ab][1]benzazepine
7. (±)-trans-3-cinnamyl-1,2,3,4,4a,8,9,14a-octahydropyrido[4′,3′:2,3]indolo[1,7-ab][1]benzazepine
8. (±)-trans-3-(2-bromocinnamyl)-1,2,3,4,4a,8,9,-14a-octahydropyrido[4′,3′:2,3]indolo[1,7-ab][1]benzazepine
9. (±)-trans-3-(3-chlorocinnamyl)-1,2,3,4,4a,8,9,-14a-octahydropyrido[4′,3′:2,3]indolo[1,7-ab][1]benzazepine
10. (±)-trans-3-(4-methoxycinnamyl)-1,2,3,4,4a,8,9,14a-octahydropyrido[4′,3′:2,3]indolo[1,7-ab][1]benzazepine
11. (±)-trans-3-(3-butenyl)-1,2,3,4,4a,8,9,14a-octahydropyrido[4′,3′:2,3]indolo[1,7-ab][1]benzazepine
12. (±)-trans-3-(2-bromoallyl)-1,2,3,4,4a,8,9,14a-octahydropyrido[4′,3′:2,3]indolo[1,7-ab]benzazepine
13. (±)-trans-3-(2-butynyl)-1,2,3,4,4a,8,9,14a-octahydropyrido[4′,3′:2,3]indolo[1,7-ab][1]benzazepine
14. (±)-trans-3-[(bicyclo[2.2.1]hept-2-en-5-yl)methyl]-1,2,3,4,4a,8,9,14a-octahydropyrido[4′,3′:2,3]indolo[1,7-ab][1]benzazepine
15. (±)-trans-3-[(2,5-cyclopentadien-1-yl)methyl]-1,2,3,4,4a,8,9,14a-octahydropyrido[4′,3′:2,3]indolo[1,7-ab][1]benzazepine
16. (±)-trans-3-[(2,4-cycloheptadien-1-yl)methyl]-1,2,3,4,4a,8,9,14a-octahydropyrido[4′,3′:2,3]indolo[1,7-ab][1]benzazepine
17. (±)-trans-3-[(3-cyclopenten-1-yl)methyl]-1,2,3,3,4a,8,9,14a-octahydropyrido[4′,3′:2,3]indolo[1,7-ab][1]benzazepine
18. (±)-trans-3-[(cis-1,6-dimethyl-endo-3-norcaren-7-yl)methyl]-1,2,3,4,4a,8,9,14a-octahydropyrido[4′,-3′:2,3]indolo[1,7-ab][1]benzazepine
19. (±)-trans-1,2,3,4,4a,8,9,14a-octahydro-3-phenacylpyrido[4′,3′:2,3]indolo[1,7-ab][1]benzazepine
20. (±)-trans-1,2,3,4,4a,8,9,14a-octahydro-3-(3-phenyl-2-propynyl)pyrido[4′,3′:2,3]indolo[1,7-ab][1]benzazepine The compounds of this invention exhibit analgesic activity and sedative-tranquilizer effects. The analgesic activity is demonstrated by the Phenylquinone Writhing (PQW) test and the sedative-tranquilizer effects are demonstrative in the results of the rodent screen. The procedures used are described as follows: Primary Rodent Screens Decreased Locomotor Activity (L.M.A.)

Results given in:mg/kg po/mouse

This reaction sign is measured subjectively by observing how an animal behaves when it is removed from an observation cage and placed on a table top. Untreated animals will immediately begin active exploration of their environment. Animals that have received a depressant compound will show a gradually decreasing responsiveness to a new environment. The degree of stimulation by the observer needed to produce active locomotion is rated on an arbitrary scale. This ranges from a score of −1 where only a slight touch of the animal's body is required to a −4 where the animal is unresponsive or minimally responsive to the application of a pain stimulus (pressure at the base of the tail). The $ED_{50}$ is the oral dose producing an obvious decrease of locomotor activity (with a score of at least −1). Groups of 5 mice are given decreasing oral doses at 0.5 log intervals (300, 100, 30...etc.) until no behavioral effects are evident. Decrease of locomotor activity is indicative of general central nervous system depressant activity.

Ptosis (Pto.)

Results given in: mg/kg po/mouse

Degree of eyelid closure is used as a measure of central nervous system depression. An animal is removed from its observation cage and allowed to remain outside the cage for 30 seconds. At the end of this time a rating of degree of eyelid closure is made on an arbitrary scale. Passive ptosis, i.e., eye closure that can be temporarily reversed by handling, is generally indicative of sedative activity for a psychotropic compound. (Active ptosis, i.e., eyelid closure that remains unchanged with handling is generally suggestive of a adrenergic blocking activity. It is a relatively rarely seen phenomenon). Only passive ptosis was observed for these compounds, the $ED_{50}$ for which is reported.

Catalepsy (Cat.)

Results given in: mg/kg po/mouse

The ability of an animal to remain in an abnormal position is used as another indication of central nervous system depressant activity. A test animal is removed from its observation cage and positioned so that its hind legs are on the table top and its front legs rest on the side of the observation cage. If an animal maintains this position for at least 10 seconds, it is considered to be showing cataleptic behavior.

The analgesic activity of the compounds of the present invention is conveniently determined in a phenylquinone writhing test, as described below:

Phenylquinone Writhing (P.Q.W.):

results given in: mg/kg po/mouse

Groups of at least 10 mice are given phenyl-p-benzoquinone 2.5 mg/kg intraperitoneally 30 minutes after oral administration of graded doses of the test substance. Two or more dose levels are used for each compound. For scoring purposes, a "writhe" is defined as stretching, twisting of a hindleg inward, or contraction of the abdomen. The total number of writhes for each animal, treated and control animals side-by-side, are counted over a 30-minute time interval. An $ED_{50}$, calculated on basis of the percentage of animals at each dose level which showed 50% or less of the average number of writhes of the control animals, is reported for each compound submitted to this screening test. The P.Q.W. test is widely used as an indicator of potential analgesic activity in man, especially for non-narcotic substances.

The results obtained with some compounds of this invention are presented in the Table below, in which codeine and chlorpromazine are used as the standards for comparison.

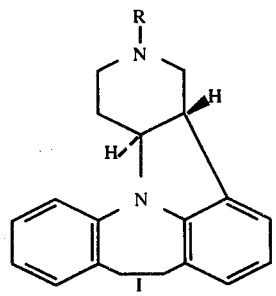

| Compound | L.M.A. | Cat. | Pto. | $LD_{50}$ | P.Q.W. |
|---|---|---|---|---|---|
| I, R = —CH₂—C≡CH | >300 | >300 | >300 | >300 | 86 |
| I, R = —CH₂—CH=C(Cl)—CH₃ | 36 | 112 | 36 | >300 | 2 |
| I, R = —CH₂—C(=O)—CH₃ | 2 | 15 | 4 | >300 | 2 |
| I, R = —CH₂—CH=CH₂ (HCl) | 7 | 11 | 11 | >300 | 1 |
| I, R = —CH₂—CH₂—C(=O)—CH₃ | 8 | 5.6 | 7.1 | >324 | 1.25 |
| I, R = —CH₂—CH=C(—CH₃)—, hydrochloride salt | 2.6 | 4.4 | 1.3 | >324 | 1.4 |
| I, R = —CH₂—CH₂—C(=O)—C₆H₅ | 200 | 300 | 20 | >324 | 26 |

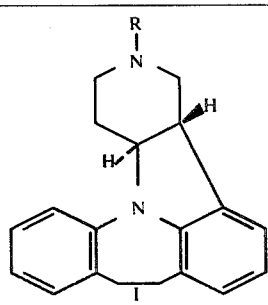

| Compound | L.M.A. | Cat. | Pto. | LD$_{50}$ | P.O.W. |
|---|---|---|---|---|---|
| hydrochloride salt chlorpromazine (HCl) | 5 | 6 | 6 | — | — |
| codeine phosphate | — | — | — | — | 19 |

The free amines of formula I and some of their pharmaceutically acceptable inorganic or organic acid addition salts are substantially insoluble in water. As CNS depressants, they are best administered orally at a level of about 0.1 to about 10 milligrams per kilogram of body weight of the animal. Some addition salts of the compounds having formula I are more water-soluble and can be administered by subcutaneous or intramuscular injection. The dosage employed in such cases generally would be within the range of about 0.02 to about 5 milligrams per kilogram of body weight.

As analgesics, the compounds of this invention are administered orally at a level of about 0.1–10 mg/kg or parenterally at the rate of about 0.05–5 mg/kg of body weight.

The compounds of the present invention can be formulated into compositions comprising a compound of formula I together with a pharmaceutically acceptable carrier. The carrier may be either a solid or liquid, and the compositions can be in form of tablets, liquid-filled capsules, dry filled capsules, aqueous solutions, non-aqueous solutions, suppositories, syrups, suspensions, and the like. The compositions can contain suitable preservatives, coloring and flavoring agents. Some examples of the carriers which can be used in the preparation of the products of the invention are gelatin capsules; sugars such as lactose and sucrose; starches; dextrans and cellulosics, such as methyl cellulose and cellulose acetate phthalate; gelatin; talc; stearic acid salts; vegetable oils such as peanut oil, sesame oil, olive oil, corn oil and oil of theobroma; liquid petrolatum; polyethylene glycol; glycerine; sorbitol; propylene glycol; ethanol; agar; water and isotonic saline.

In preparing the compositions of the invention for pharmaceutical uses, the conventional practices and precautions are used. The composition intended for parenteral administration must be sterile, and this can be accomplished either by using sterile ingredients and carrying out the production under aseptic conditions, or by sterilizing the final composition by one of the usual procedures such as autoclaving under appropriate temperature and pressure conditions. Customary care should be exercised that no incompatible conditions exist between the active components and the diluent preservative or flavoring agent or in the conditions employed in preparation of the compositions.

The compositions of the invention can be introduced into warm-blooded animals by the oral, rectal or parenteral route. This can be done by swallowing, in the case of liquid or solid preparations; by suppositories; or by injecting the liquid preparations intraveneously, intramuscularly, intraperitoneally, or subcutaneously.

The compounds of this invention are administered to warm-blooded animals to produce the desired pharmacologic response. Dosage forms are prepared at various strengths depending on the potency of the compound and the desired effect. It is possible, for example, to estimate the probable human dose for analgesia by comparing the animal analgetic dose for the compound of this invention to the dose of a standard drug in the same animal system. Thus, the compound of Example 2 is shown to have analgesic activity compared to codeine phosphate.

|  | Analgesic ED$_{50}$ | Usual Human Dose | Dosage Form Strength |
|---|---|---|---|
| Codeine phosphate | 19 mg/kg | 15–300 mg/day | 15–60 mg |
| Compound of Example 4 | 1 mg/kg | 1–15 mg/day | 1–15 mg. |

Since the compound of Example 4 is about 20X more potent than codeine phosphate its human dose is estimated to be 1–15 mg/day (1/20 the codeine dose). Dosage forms of the compound will ordinarily contain 1 to 15 mg of the active ingredient, however lower or higher strengths may be required depending on the age and condition of the patient being treated, the severity of the pain and the frequency of treatment required.

In a similar manner, by comparing the effects of a standard drug like chlorpromazine in the same animal systems as the compounds of this invention, the strengths of dosage forms for human use may be determined.

|  | LMA | Catalepsy | Ptosis | Usual Human Dose | Dosage Form Strength |
|---|---|---|---|---|---|
| Chlorpromazine | 5 | 6 | 6 | 10–1000 mg/day | 10–200 mg |
| Compound of Example 3 | 2 | 15 | 4 | 10–1000 mg/day | 10–200 mg |
| Compound of | | | | | |

-continued

|  | LMA | Catalepsy | Ptosis | Usual Human Dose | Dosage Form Strength |
|---|---|---|---|---|---|
| Example 4 | 7 | 11 | 11 | 10–1000 mg/day | 10–200 mg |

Since the above compounds of this invention are similar in potency to chlorpromazine in animal tests, the human doses are estimated to be similar to those recommended for chlorpromazine.

Typical formulations of the type listed above which may be used for the administration of these compounds are:

Example A

| Ingredients | mg/tablet |
|---|---|
| 3-(allyl)-1,2,3,4,4a,8,9,14a-octa = hydropyrido[4',3' : 2,3]indolo[1,7-ab]= [1]benzazepine | 15 mg. |
| lactose, USP | 185 mg. |

All of the above ingredients are passed through a suitable sieve, blended for 20 minutes, and compressed directly into tablets of 200 mg on a suitable tablet press using a 11/32" punch and die.

Example B

| Ingredients | mg/tablet |
|---|---|
| 3-(3-chloro-2-butenyl)-1,2,3,4,4a,8, = 9,14a-octahydropyrido[4',3' : 2,3]indolo = [1,7-ab][1]benzazepine hydrochloride | 50 mg |
| lactose, USP | 215 mg |
| methylcellulose, USP | 15 mg |
| talc, USP | 6 mg |
| starch, USP | 10 mg |
| magnesium stearate, USP | 4 mg |
| color (if desired) | q.s. |

The lactose and active ingredient are wet granulated with a solution of methylcellulose in a blender until a satisfactory mass is achieved. The mass is dried and classified through an appropriate sieve. The remaining ingredients are passed through an 80 mesh sieve and blended with the dried granulated material. The blend is then compressed into tablets on a suitable tablet press at a weight of 300 mg using a ⅜ inch punch and die.

Example C

| Ingredients | mg/capsule |
|---|---|
| 3-acetonyl-1,2,3,4,4a,8,9,14a-octahydro = pyrido[4',3' : 2,3]indolo[1,7-ab][1]benza = zepine | 25 mg |
| lactose, USP | 100 mg |
| magnesium stearate, USP | 1 mg |
| colloidal silicon dioxide, N.F. | 2 mg |

The combined ingredients are blended and passed through a 40 mesh sieve, and the mixture is encapsulated into a two-piece hard gelatin No. 3 capsule on a suitable encapsulating machine at a net weight of 128 mg.

I claim:
1. Compounds of the formula wherein
n is zero or one;
X is the anion of a pharmaceutically suitable acid; and
R is 3-chloro-2-butenyl: $C_3$-$C_8$ oxoalkyl side chain; phenacyl; 3-oxo-3-phenylpropyl; $C_3$-$C_5$ alkenyl; $C_3$-$C_5$ alkynyl; or $C_6$-$C_8$ cycloalkenylmethyl; and the hydrogens in the 4a and 14a positions are in trans relationship to each other.
2. Compounds of claim 1 wherein
R is 3-chloro-2-butenyl; acetonyl; phenacyl; $C_3$-$C_5$ alkenyl: $C_3$-$C_5$ alkynyl; or $C_6$-$C_8$ cycloalkenylmethyl.
3. Compounds of claim 1 wherein
R is 3-chloro-2-butenyl; $C_3$-$C_8$ oxoalkyl side chain; phenacyl; 3-oxo-3-phenylpropyl; $C_3$-$C_5$ alkenyl; $C_3$-$C_5$ alkynyl; or $C_6$-$C_8$ cycloalkenylmethyl.
4. Compounds of claim 3 wherein the oxoalkyl side chain is a ketoalkyl side chain.
5. Compounds of claim 4 wherein the ketoalkyl side chain has from 3 to 5 carbon atoms.
6. Compound of claim 4 wherein R is a $C_3$-$C_5$ ketoalkyl aide chain; phenacyl; or 3-oxo-3-phenylpropyl.
7. Compound of claim 1 wherein n is zero and R is 3-chloro-2-butenyl.
8. Compound of claim 1 wherein n is zero and R is 2-propynyl.
9. Compound of claim 1 wherein n is zero, and R is acetonyl.
10. Compound of claim 1 wherein n is one, X is Cl, and R is allyl.
11. Compound of claim 1 wherein n is zero and R is 3-oxobutyl.
12. Compound of claim 1 wherein n is one, X is chlorine, and R is 4-oxopentyl.
13. Compound of claim 1 wherein n is one, X is chlorine, and R is 3-oxo-3-phenylpropyl.
14. A pharmaceutical composition consisting essentially of a pharmaceutically suitable vehicle and means for producing an analgetic effect selected from compounds of claim 1.
15. A method for producing an analgetic effect in a warm-blooded animal comprising administering to said animal an analgetically-effective amount of a compound of claim 1.
16. A method of producing a sedative tranquilizer effect in a warm-blooded animal which comprises administering to said animal an effective amount of a compound of claim 1 wherein R is 3-chloro-2-butenyl 2-oxopropyl, 3-oxobutyl, 4-oxopentyl or allyl.

* * * * *

UNITED STATES PATENT OFFICE
CERTIFICATE OF CORRECTION

PATENT NO. : 4,018,930
DATED : April 19, 1977
INVENTOR(S) : Joel G. Berger

It is certified that error appears in the above-identified patent and that said Letters Patent are hereby corrected as shown below:

At column 3, line 12,

Insert a parenthesis between the words "immediately" and "trans";

At column 11, the third compound from the bottom should read:

Signed and Sealed this

Eleventh Day of October 1977

[SEAL]

Attest:

RUTH C. MASON
Attesting Officer

LUTRELLE F. PARKER
Acting Commissioner of Patents and Trademarks